United States Patent
Lloret Soler et al.

(10) Patent No.: US 9,310,185 B2
(45) Date of Patent: Apr. 12, 2016

(54) ELECTRO-OPTICAL SILICON-BASED PHASE MODULATOR WITH NULL RESIDUAL AMPLITUDE MODULATION

(71) Applicant: MEDLUMICS, S.L., Madrid (ES)

(72) Inventors: Juan Lloret Soler, Tres Cantos (ES); Kirill Zinoviev, Tres Cantos (ES); José Luis Rubio Guivernau, Madrid (ES); Eduardo Margallo Balbás, Tres Cantos (ES)

(73) Assignee: Medlumics, S.L., Madrid (ES)

( * ) Notice: Subject to any disclaimer, the term of this patent is extended or adjusted under 35 U.S.C. 154(b) by 0 days.

(21) Appl. No.: 14/299,725

(22) Filed: Jun. 9, 2014

(65) Prior Publication Data

US 2014/0368828 A1    Dec. 18, 2014

Related U.S. Application Data

(60) Provisional application No. 61/834,297, filed on Jun. 12, 2013.

(51) Int. Cl.
*G02F 1/035* (2006.01)
*G01B 9/02* (2006.01)
*G02F 1/025* (2006.01)
(Continued)

(52) U.S. Cl.
CPC .......... *G01B 9/02091* (2013.01); *G01B 9/0201* (2013.01); *G02F 1/025* (2013.01); *G02F 1/2257* (2013.01); *A61B 5/0066* (2013.01);
(Continued)

(58) Field of Classification Search
CPC .... G02F 1/015; G02F 2001/0151–2001/0154; G02F 1/025; G02F 2203/50; G02F 1/2257; G02B 2006/12142; G01B 9/02091; G01B 9/0201; A61B 5/0066

USPC ........................................................ 385/1–3
See application file for complete search history.

(56) References Cited

U.S. PATENT DOCUMENTS 5,566,381 A * 10/1996 Korotky ...................... 398/147
5,787,211 A * 7/1998 Gopalakrishnan ............... 385/2
(Continued)

FOREIGN PATENT DOCUMENTS

JP    2010-161646    *    7/2010    ............. H04B 10/02

OTHER PUBLICATIONS

Soref et al., Electrooptical Effects in Silicon, ISEE Journal of Quantum Electronics, vol. QE-23, No. 1, Jan. 1987, 7 pages.
(Continued)

*Primary Examiner* — Robert Tavlykaev
(74) *Attorney, Agent, or Firm* — Sterne, Kessler, Goldstein & Fox P.L.L.C.

(57) ABSTRACT

Systems and methods are presented for modulating a beam of radiation, such that the modulated beam exhibits substantially null residual amplitude modulation (RAM). An electro-optical modulator is presented that includes a waveguide, a first region associated with the waveguide and a second region associated with the waveguide. The waveguide is designed to guide a beam of radiation. A first electric potential applied to the first region causes a first modulation to the beam of radiation while a second electric potential applied to the second region causes a second modulation to the beam of radiation. The first modulation combined with the second modulation provides substantially null residual amplitude modulation of the beam of radiation.

17 Claims, 12 Drawing Sheets

(51) Int. Cl.
 *G02F 1/225* (2006.01)
 *G02B 6/12* (2006.01)
 *A61B 5/00* (2006.01)

(52) U.S. Cl.
 CPC ... *G02B2006/12142* (2013.01); *G02F 2201/06* (2013.01); *G02F 2203/50* (2013.01)

(56) References Cited

U.S. PATENT DOCUMENTS

| | | | |
|---|---|---|---|
| 5,975,697 A * | 11/1999 | Podoleanu et al. | 351/206 |
| 7,092,609 B2 * | 8/2006 | Yegnanarayanan et al. | 385/131 |
| 7,167,293 B2 | 1/2007 | Piede | |
| 2005/0036150 A1 | 2/2005 | Izatt et al. | |
| 2006/0171013 A1 * | 8/2006 | Piede | 359/279 |
| 2008/0198367 A1 | 8/2008 | Chang et al. | |
| 2010/0253948 A1 * | 10/2010 | Strandjord | G01C 19/727 356/464 |
| 2011/0136288 A1 * | 6/2011 | Duane et al. | 438/59 |
| 2011/0164302 A1 | 7/2011 | Quetschke et al. | |
| 2012/0003767 A1 | 1/2012 | Fujikata et al. | |
| 2012/0251032 A1 | 10/2012 | Kato | |

OTHER PUBLICATIONS

International Search Report directed to related International Patent Application No. PCT/EP2014/062146, mailed Aug. 11, 2014; 5 pages.

Written Opinion of the International Preliminary Searching Authority directed to related International Patent Application No. PCT/EP2014/062146, mailed Jun. 17, 2015; 7 pages.

* cited by examiner

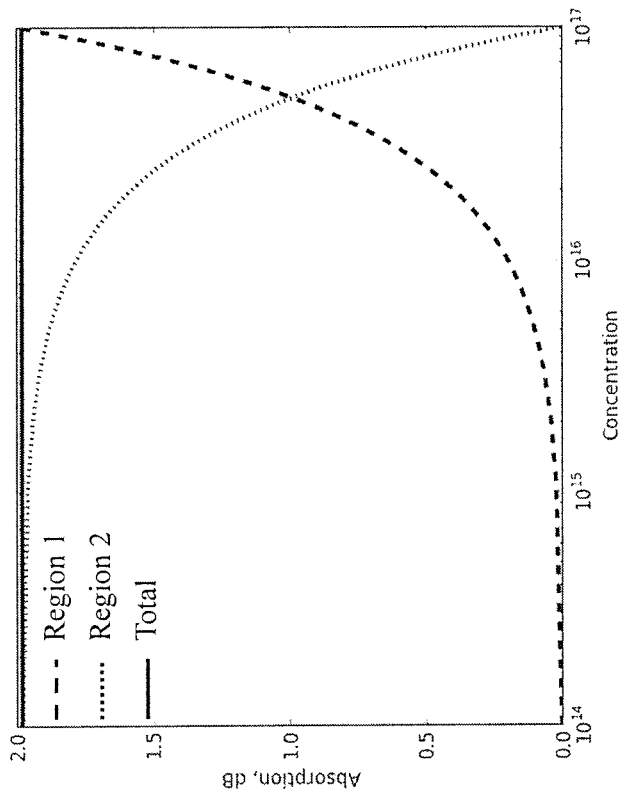
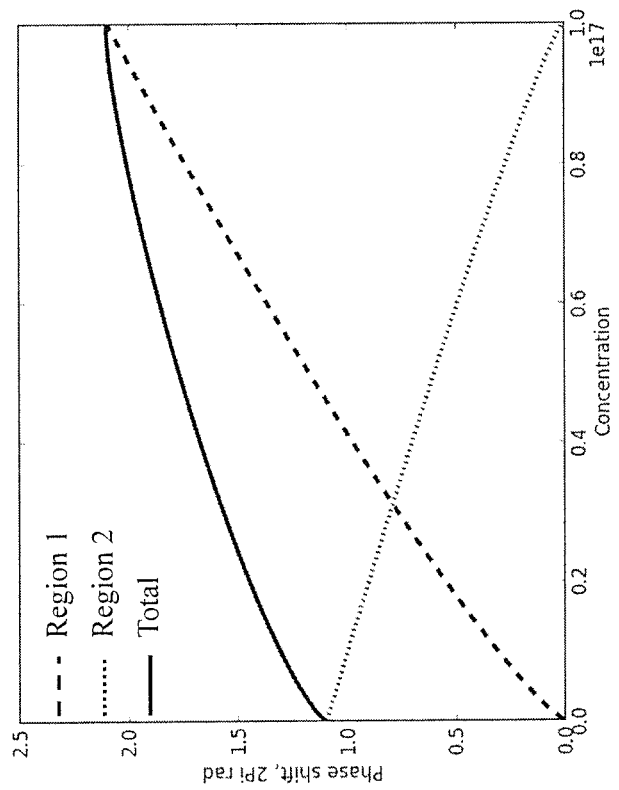
FIG. 7A
FIG. 7B

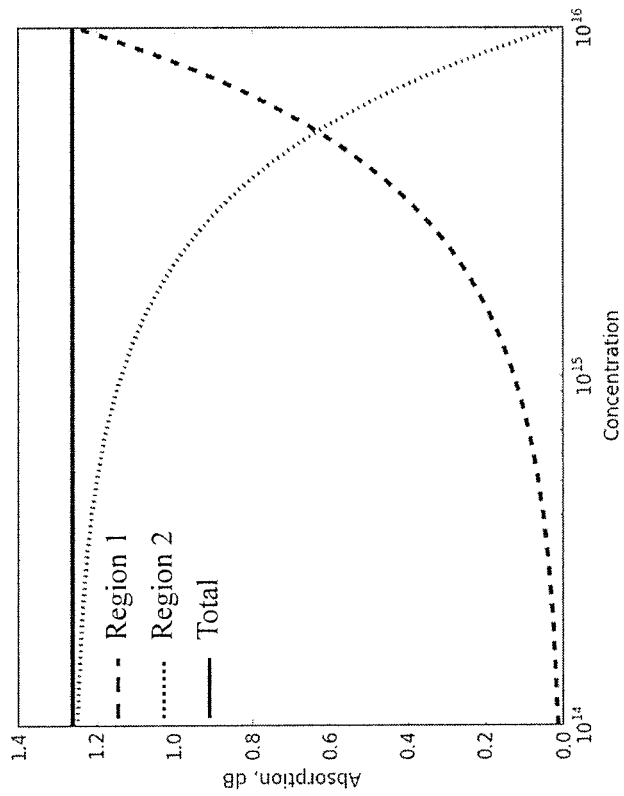
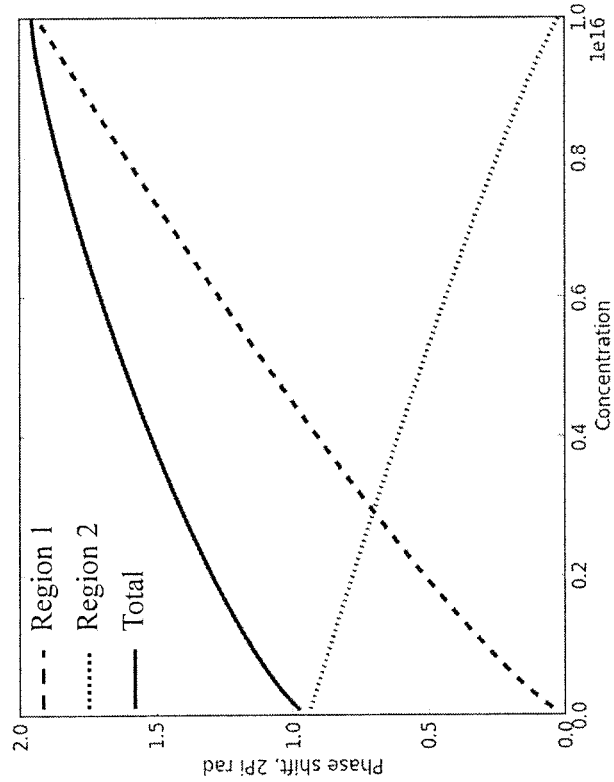
FIG. 8A
FIG. 8B

ELECTRO-OPTICAL SILICON-BASED PHASE MODULATOR WITH NULL RESIDUAL AMPLITUDE MODULATION

This application claims the benefit under 35 U.S.C. §119(e) to U.S. Appl. No. 61/834,297, filed Jun. 12, 2013, the disclosure of which is incorporated by reference herein in its entirety.

BACKGROUND

1. Field

Embodiments of the invention relate to designs of, and methods of using, an electro-optical phase modulator for use in an optical coherence tomography system.

2. Background

Optical Coherence Tomography (OCT) is a medical imaging technique providing depth resolved information with high axial resolution by means of a broadband light source and an interferometric detection system. It has found plenty of applications, ranging from ophthalmology and cardiology to gynecology and in-vitro high-resolution studies of biological tissues.

A common element found in both OCT systems and optical communication networks is a phase modulator designed to shift the phase and/or frequency of a beam of light. In a basic phase modulation (PM) scheme, the information of the modulating signal is transferred into the optical signal in the form of instantaneous phase variations, which translates into instantaneous frequency modulation. PM has been exploited in all-optical circuits finding application in various other fields, including signal processing, sensing and biophotonics.

Several technologies have been demonstrated as suitable for implementing PM of light. Among them, those implemented by Photonic Integrated Circuits (PICs) are useful since complete manufacturing on a single substrate using techniques similar to those found in microelectronics is feasible. As a result, final devices featuring a small footprint, high stability and reliability, and reduced manufacturing costs can be achieved. PM on PICs has been traditionally implemented by exploiting the Pockels effect in lithium niobate (LiNbO3). However, other technologies based on carrier recombination in indium phosphide (InP), silicon-on-insulator (SOI), liquid crystals (LC), polymers and the hybridization of materials such as III-V group materials on silicon or silicon-polymer mixtures have emerged in the past few years.

There exist two different physical mechanisms governing refractive index modulation in SOI structures. The first mechanism is the thermo-optic (TO) effect. The refractive index in silicon has a dependence on the temperature that stems from the lattice constant's dependence on the temperature. This effect translates into changes in the optical properties of the material thus modifying its refractive index. In particular, the TO coefficient in SOI is defined as $dn/dT = 2.4 \cdot 10^{-4}$ $K^{-1}$, with n being the refractive index and T being the temperature. The amplitude variation of the optical signal propagating through the SOI structure is negligible when modifying the temperature since it has a reduced influence on the imaginary part of the refractive index. This implies that no extra absorption is derived from the modulation process. However, the TO dynamics are typically limited to the scale of several tens to hundreds of microseconds, resulting in maximum operating rates in the order of tens to hundreds of kilohertz. Such operating rates may not be fast enough for certain imaging techniques based on OCT.

The second mechanism governing refractive index modulation in SOI structures is known as the plasma dispersion (PD) effect. The PD effect is based on the injection or depletion of free carriers into the intrinsic silicon comprising the SOI waveguide structure. The free carrier concentration has strong influence on both the imaginary and real parts of the refractive index of the material. The efficiency of the refractive index change for the PD effect is higher compared with the TO effect, since larger modifications can be reached in the real part of the refractive index. However, the mentioned variations in the real part are accompanied by a change in its imaginary part as well, resulting in extra light absorption owing to the carrier density modulation. Consequently, due to the extra light absorption, the PD effect in silicon induces a Residual Amplitude Modulation (RAM) to the modified signal. A solution consisting of filtering out the output modulated signal has been proposed in U.S. Pat. No. 7,167,293 for the purpose of reducing the RAM in PD-based SOI optical modulators. However, to completely mitigate the RAM, perfect topology symmetry and fine tuning of the filters are required. As a result, the perfect mitigation of the RAM becomes challenging and its effect can still be high enough to drown out small signal variations carrying important information for some applications.

BRIEF SUMMARY

A system that uses the PD effect to modulate the phase of an optical signal while suppressing RAM of the optical signal is presented. The use of the system within the scope of optical coherence tomography and the advantages gained by using such a system are also described.

In an embodiment, an electro-optical modulator is presented that includes a waveguide, a first region associated with the waveguide and a second region associated with the waveguide. The waveguide is designed to guide a beam of radiation. A first electric potential applied to the first region causes a first modulation to the beam of radiation while a second electric potential applied to the second region causes a second modulation to the beam of radiation. The first modulation combined with the second modulation provides substantially null residual amplitude modulation of the beam of radiation.

In another embodiment, an electro-optical modulator is presented that includes a waveguide and a plurality of regions associated with the waveguide. The waveguide is designed to guide a beam of radiation. An electric potential is applied to each region of the plurality of regions, and each applied potential causes a respective modulation to the beam of radiation. The combination of each respective modulation provides substantially null residual amplitude modulation of the beam of radiation.

In another embodiment, an optical coherence tomography system is presented. The system includes an optical source, an optical element, and an electro-optical modulator. The optical source provides a beam of radiation. The optical element is designed to split the beam of radiation between at least a first waveguide and a second waveguide. A first portion of the beam of radiation propagates through the first waveguide and a second portion of the beam of radiation propagates through the second waveguide. The electro-optical modulator is associated with the first waveguide and includes a first region and a second region. A first electric potential applied to the first region causes a first modulation to the first portion of the beam of radiation and a second electric potential applied to the second region causes a second modulation to the first portion of the beam of radiation. The first modulation combined with the second modulation provides substantially null residual amplitude modulation of the first portion of the beam of radiation.

An example method is described. In an embodiment, the method includes guiding a beam of radiation through a waveguide. The method further includes applying a first electric potential to a first region associated with the waveguide and applying a second electric potential to a second region associated with the waveguide and cascaded with the first region. The applying of the first electric potential and the applying of the second electric potential cause a substantially null residual amplitude modulation of the beam of radiation.

In an embodiment, an electro-optical modulator is presented that includes a waveguide, a first region, and a second region. The waveguide is designed to guide a beam of radiation having an amplitude and a frequency. Both the first region and the second region are associated with the waveguide. A first electric potential applied to the first region causes a residual amplitude modulation of the beam of radiation. A second electric potential applied to the second region achieves substantially null residual amplitude modulation of the beam of radiation. At least one of the first electric potential and the second electric potential causes a modulation in the frequency of the beam of radiation.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

Figure 4B:
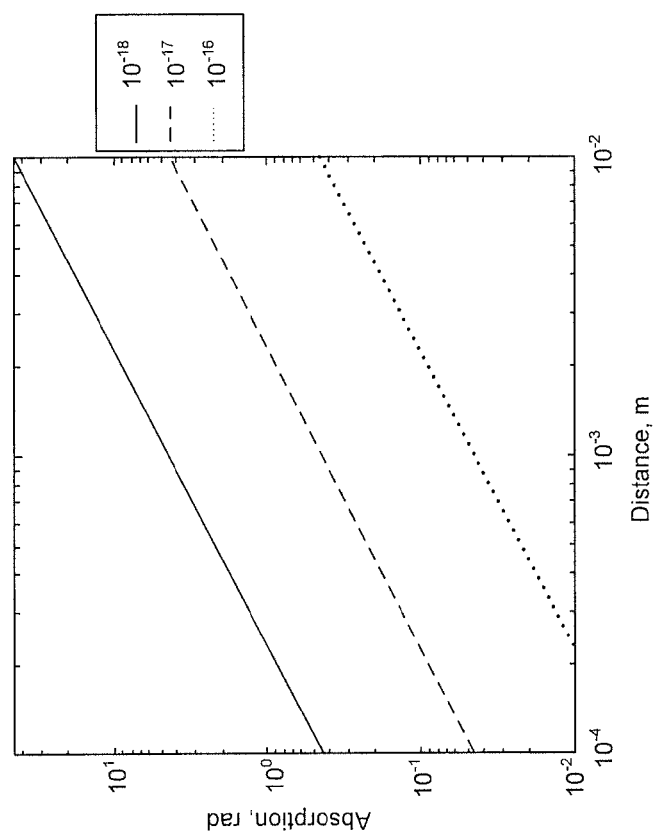
Figure 4A:
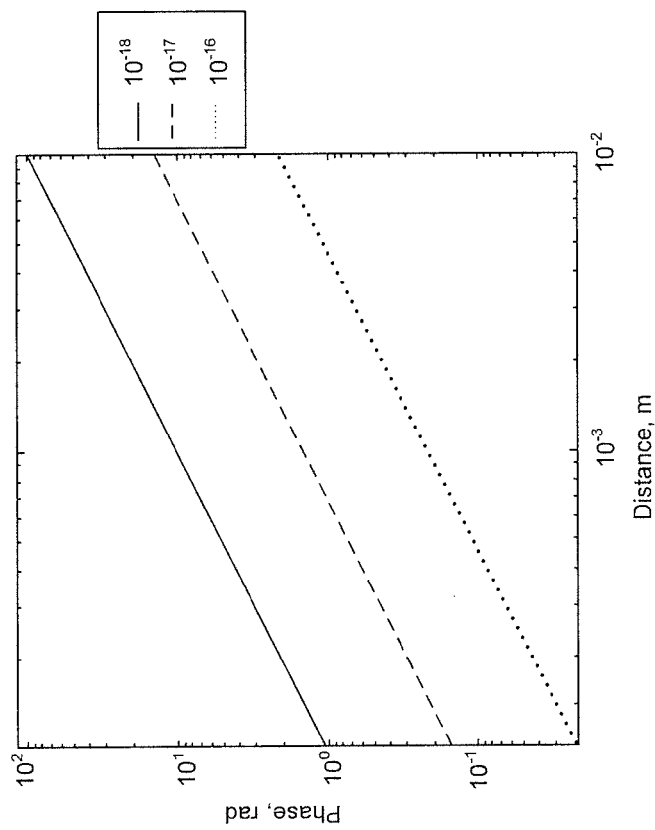

FIGS. 4A-4B display simulation results for phase and absorption vs. distance, according to some embodiments.

Figure 5:
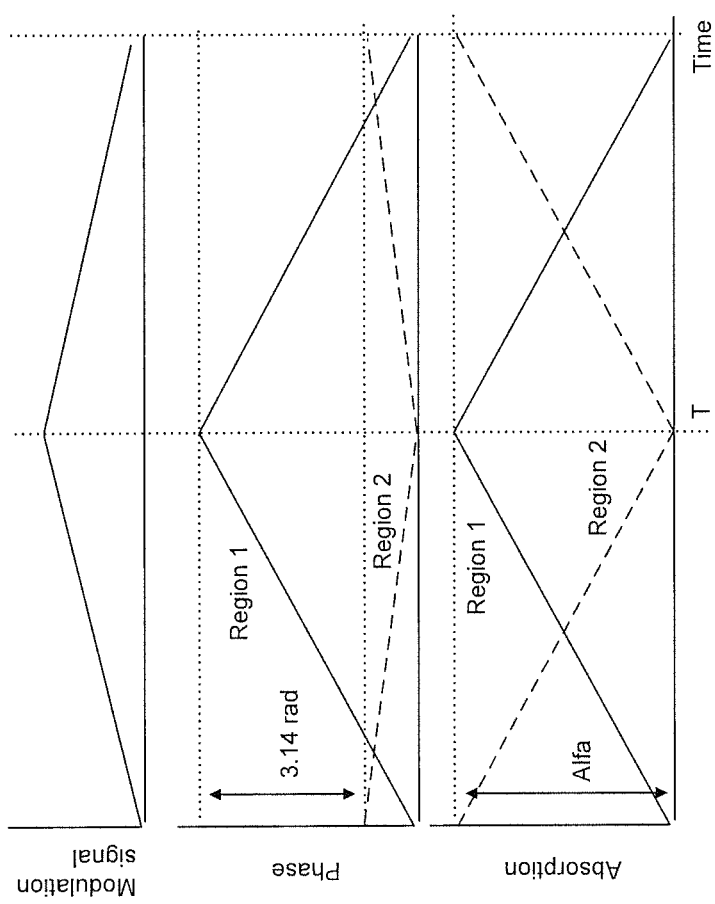

FIG. 5 displays phase and absorption results for an example modulation signal, according to an embodiment.

Figure 6A:
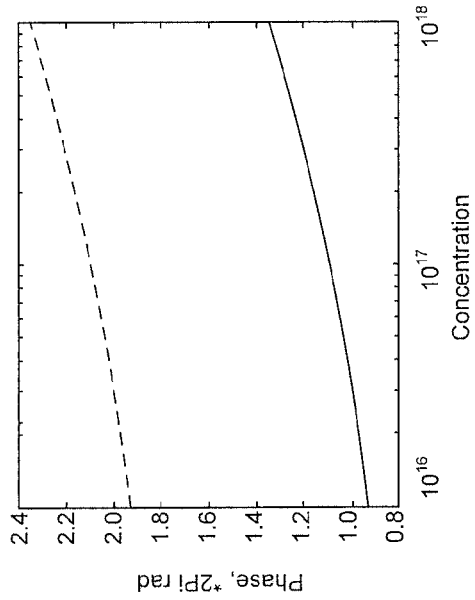
Figure 6B:
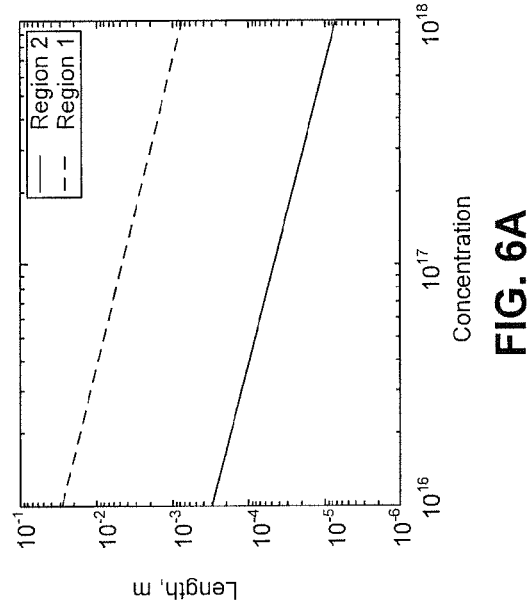
Figure 6C:
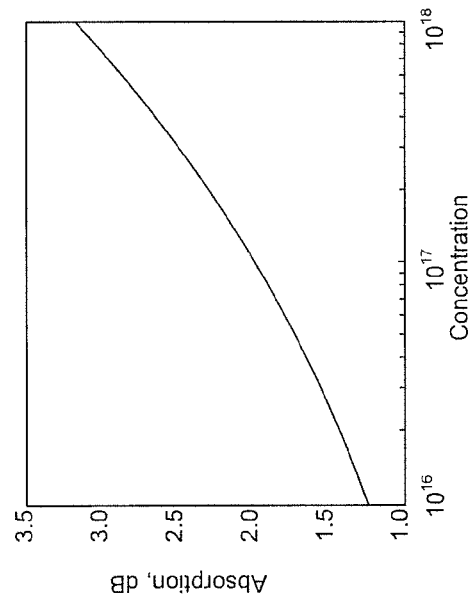

FIGS. 6A-6C display simulation results based on varying dopant concentrations, according to some embodiments.

FIGS. 7A-7B display simulation results for phase and absorption vs. dopant concentration, according to some embodiments.

FIGS. 8A-8B display simulation results for phase and absorption vs. dopant concentration, according to further embodiments.

Figure 9A:
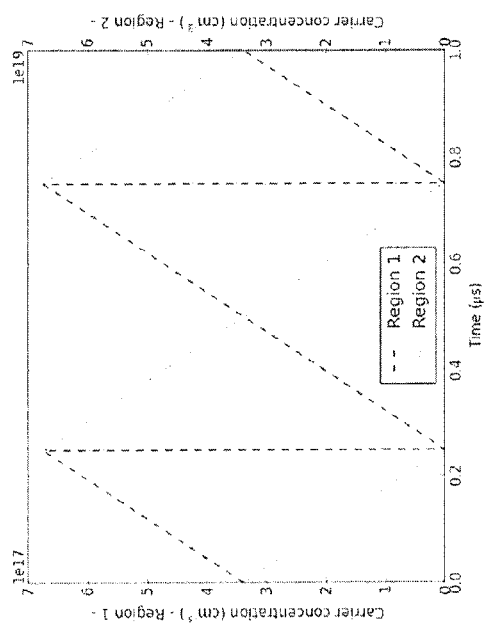
Figure 9C:
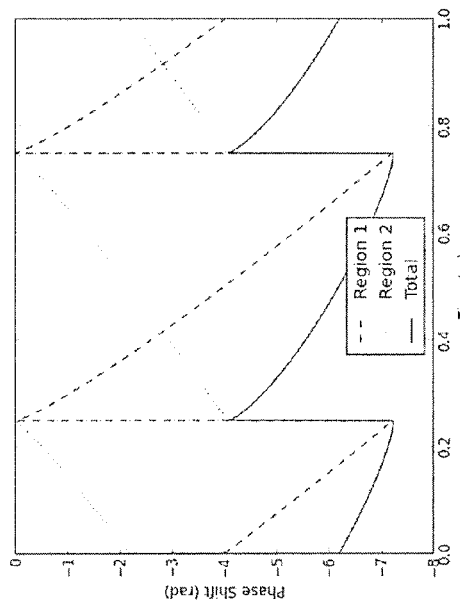
Figure 9B:
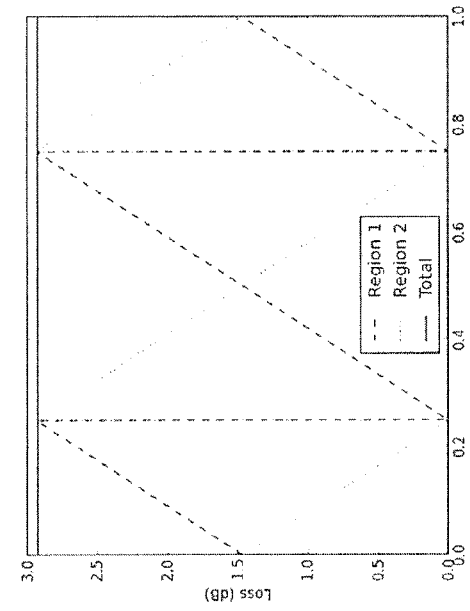

FIGS. 9A-9C display simulation results for an electro-optical modulator over time, according to some embodiments.

Figure 10:
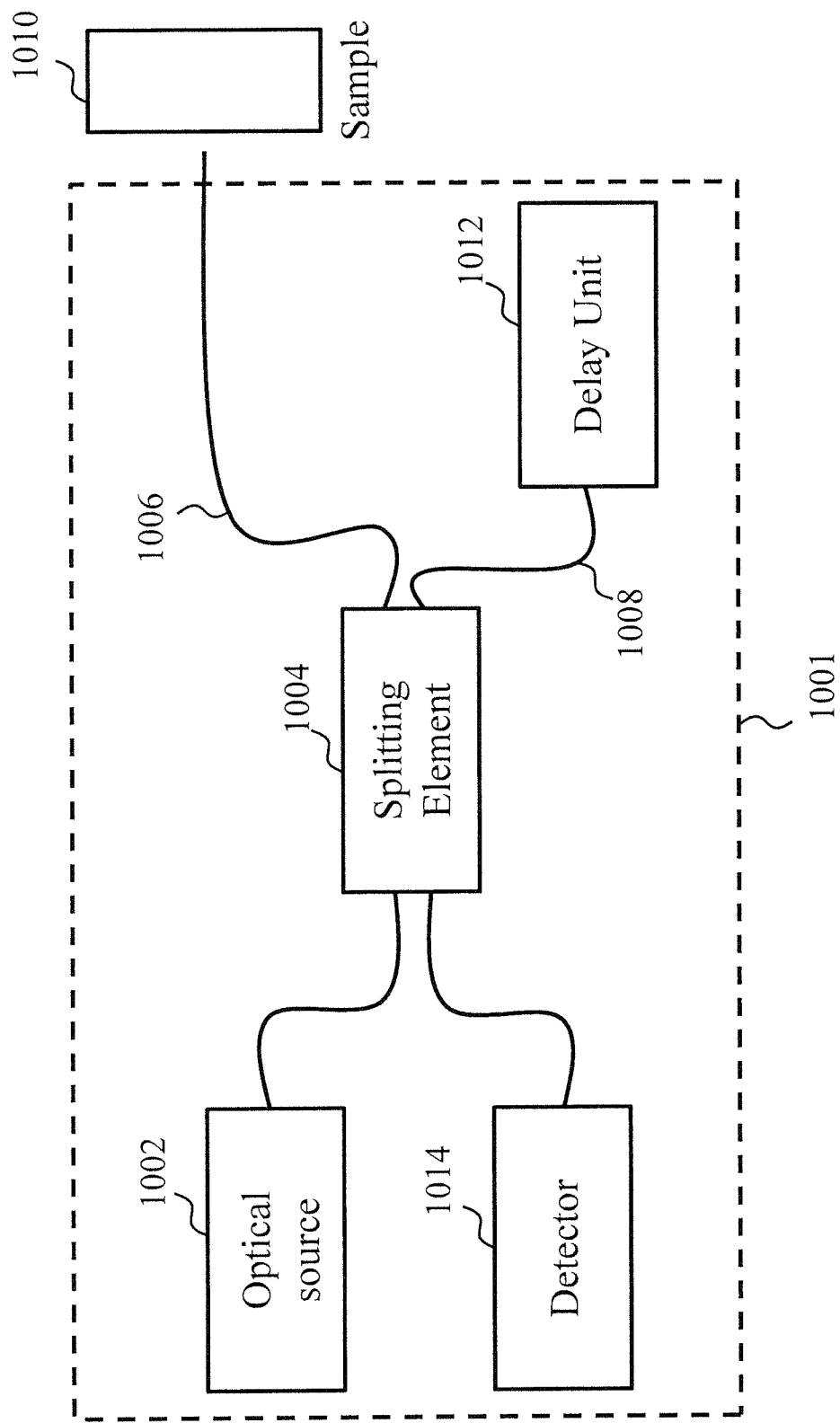

FIG. 10 illustrates a block diagram of an OCT system, according to an embodiment.

Figure 11:
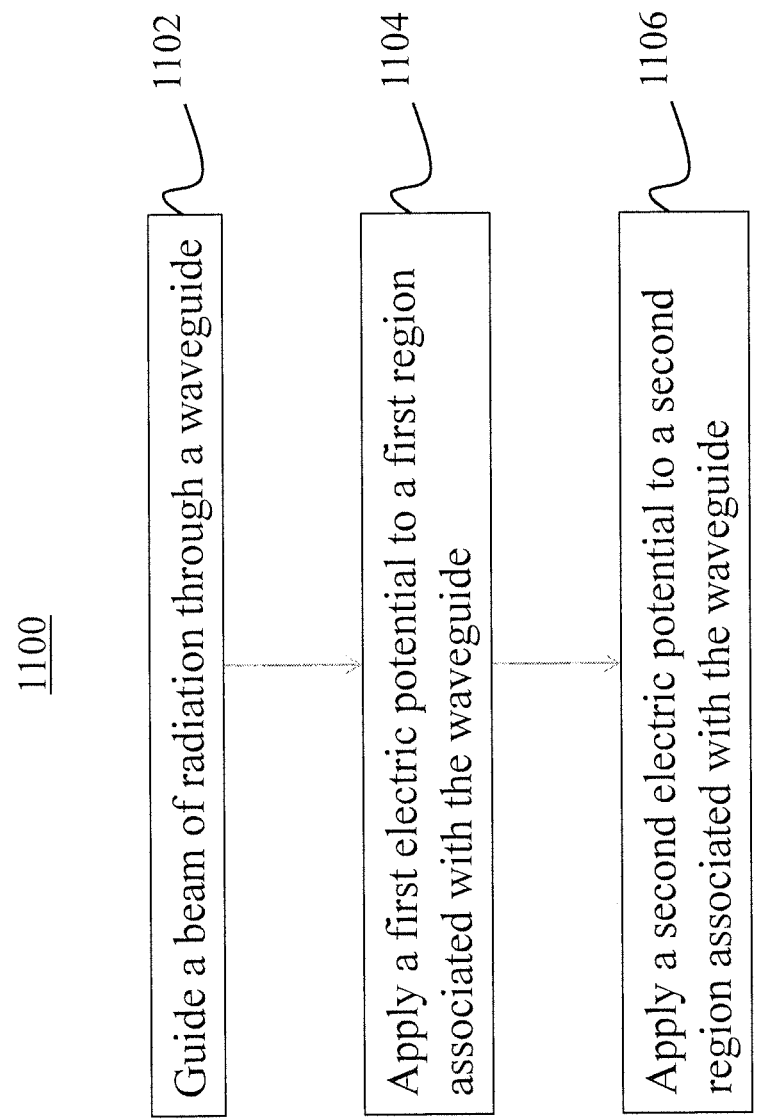

FIG. 11 depicts a method, according to an embodiment.

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Devices for performing traditional phase and frequency modulation are often found in numerous optical systems across a wide array of applications. Embodiments described herein provide systems and methods for modulating the phase and/or frequency of a beam of radiation while also substantially nullifying any residual amplitude modulation (RAM). The ability to modulate the properties of light allows for the propagation of light across long distances and advanced imaging techniques, just to name a few example applications.

One imaging technique is optical coherence tomography which utilizes interferometry, phase delay, and optical modulation to combine light in various ways in order to produce images at different depths in a sample.

Herein, the terms "electromagnetic radiation," "light," and "beam of radiation" are all used to describe the same electromagnetic signals propagating through the various described elements and systems.

Figure 1:
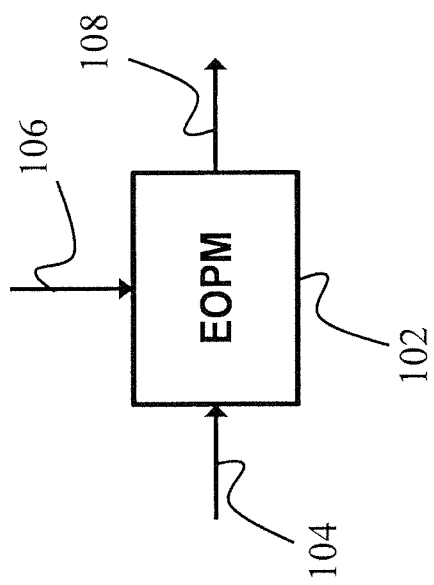
FIG. 1 illustrates an electro-optical modulator, according to an embodiment.

FIG. 1 illustrates an example of an electro-optical modulator 102, according to an embodiment. Electro-optical modulator 102 receives an input signal 104, such as, for example, a beam of electromagnetic radiation. This beam may be confined in a waveguide structure for propagating through electro-optical modulator 102. Electro-optical modulator 102 also receives a modulating signal 106. Modulating signal 106 is an electrical signal and is used to control the modulation of input signal 104. Other types of modulators may use other types of modulating signals, for example, acousto-optic modulators use acoustic or piezoelectric signals as modulating signal 106 while thermo-optic modulators use heat as modulating signal 106. The modulated beam of radiation is output from electro-optical modulator 102 as output signal 108. The information conveyed in modulating signal 106 is transferred into the phase of input signal 104. Therefore, at the output of electro-optical modulator 102, the phase of input signal 104 is modulated in accordance with modulating signal 106.

Figure 2A:
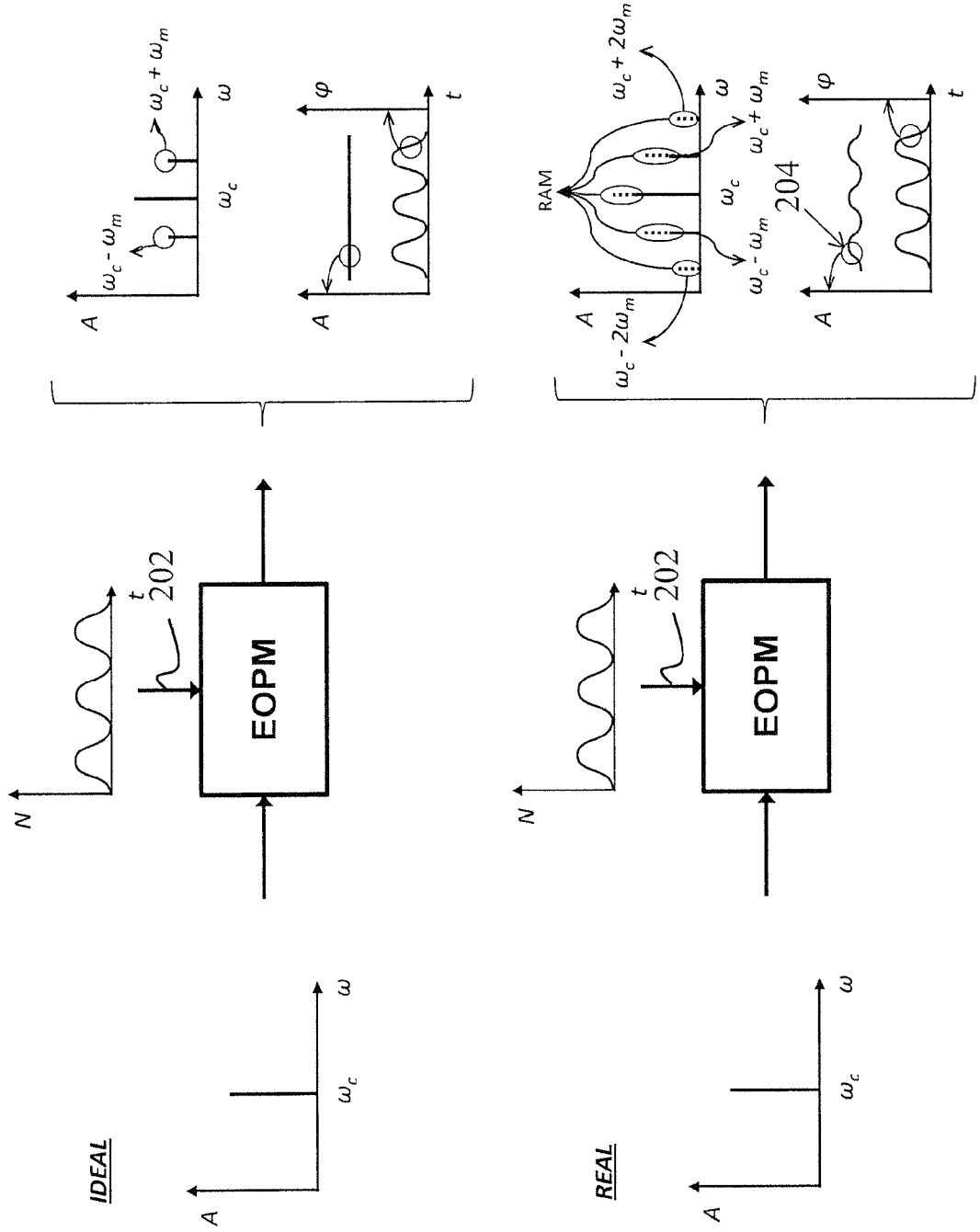
FIGS. 2A-2B illustrate ideal and real effects of an electro-optical modulator.
Figure 2B:
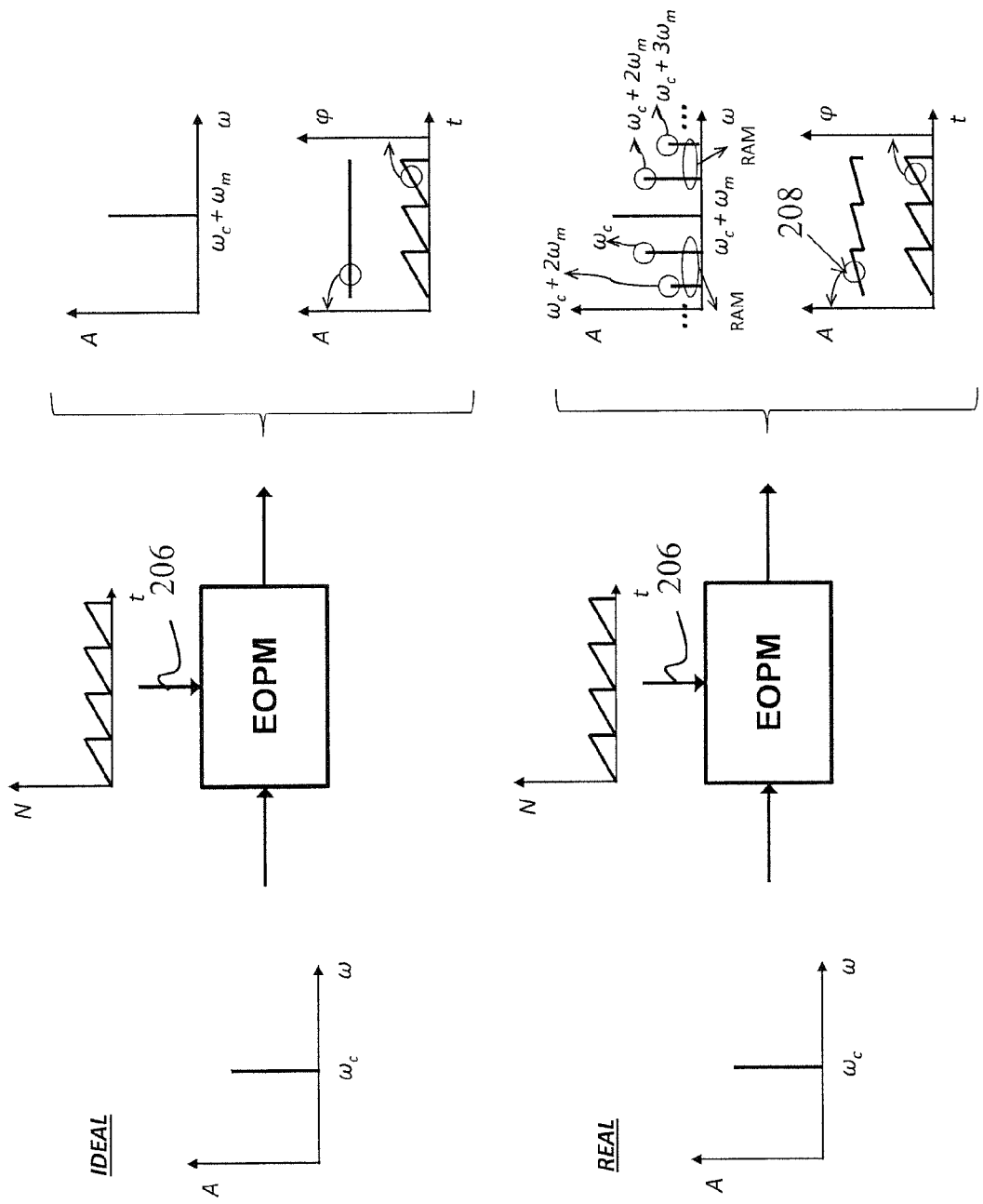

In a typical electro-optical modulator using the PD effect and implemented on an SOI substrate, modulating the phase of an input signal via carrier injection also causes an amplitude modulation (RAM) of the input signal. FIGS. 2A and 2B illustrate the effect of the RAM.

FIG. 2A illustrates using a modulating signal 202 with an electro-optical phase modulator (EOPM) to create a sinusoidal carrier density profile with time. In the "ideal" scenario, such a modulating signal produces a double-sideband signal with three optical waves at angular frequencies of $\omega_c$, $\omega_c + \omega_m$, and $\omega_c - \omega_m$, where $\omega_c$ is the frequency of the carrier signal and $\omega_m$ is the frequency of the modulating signal. In the time domain, the phase of the signal follows the modulating sinusoidal shape while the amplitude remains flat. However, in reality, the changing carrier density in the EOPM causes RAM to occur in the output signal. The RAM takes place because of the dependence of the absorption coefficient of silicon on the carrier concentration. The "real" scenario illustrates the undesired effects in both the frequency and time domains of the output signal due to RAM. A modulation 204 has been induced in the amplitude of the signal over time due to RAM. Such a modulation to the amplitude of the signal may cause signal errors in certain applications, such as when performing OCT.

FIG. 2B illustrates the use of a different modulating signal 206 with an EOPM to create a sawtooth carrier density profile with time. In the "ideal" scenario, such a modulating signal produces an output signal having a single frequency shifted to $\omega_c+\omega_m$. In the time domain, the phase of the signal follows the modulating sawtooth shape having a phase amplitude that is a multiple of $2\pi$ while the amplitude of the signal remains flat. Similarly to FIG. 2A, the "real" scenario illustrates how RAM affects the output signal. Harmonic frequencies are generated in the frequency domain while a modulation 208 has been induced in the amplitude of the signal in the time domain.

Figure 3:
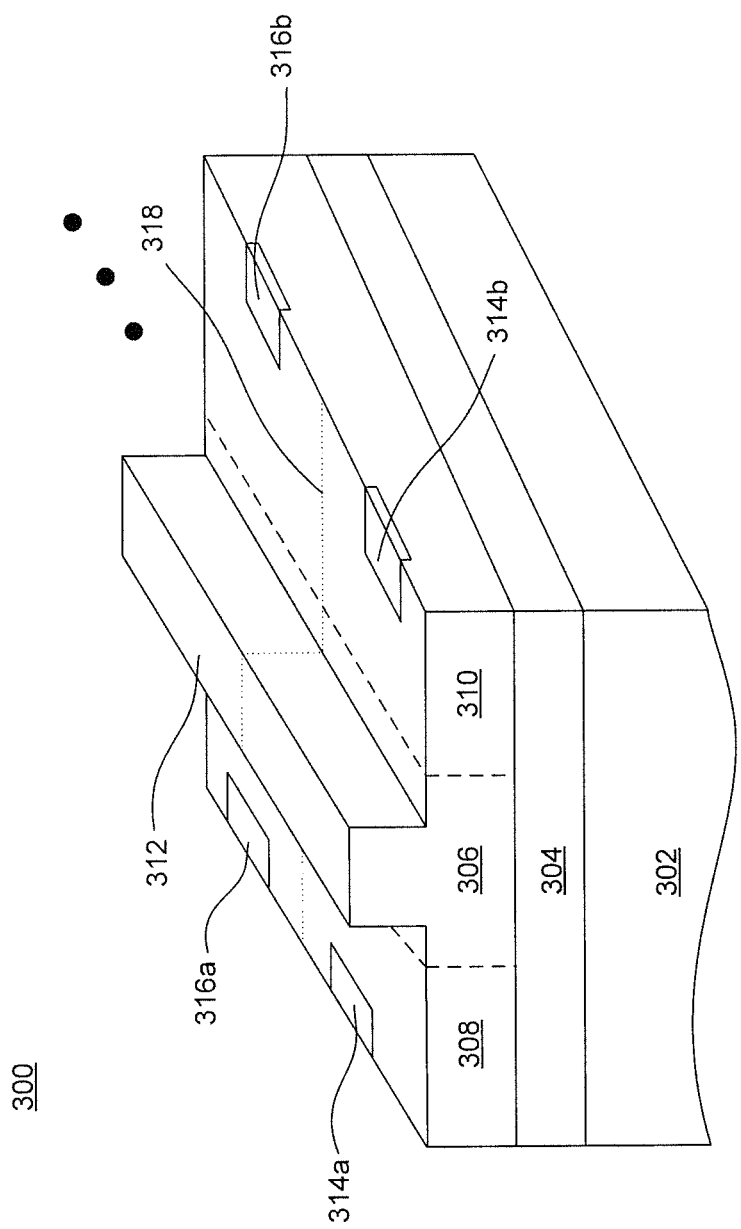
FIG. 3 illustrates a design of an electro-optical modulator, according to an embodiment.

In an embodiment, a design for an electro-optical phase modulator is described that substantially nullifies the traditionally induced RAM on the output optical signal. FIG. 3 illustrates the structure of an electro-optical phase modulator 300 on an SOI wafer, according to an embodiment. Although it is not required for the electro-optical phase modulator to be fabricated on an SOI layer structure, embodiments herein will be described using the SOI structure as an example.

Electro-optical phase modulator 300 includes a bulk semiconductor layer 302, a buried insulating layer 304 and a top semiconducting layer distinguished by doped section 308, doped section 310, and waveguiding section 306. The layer structure provides a traditional SOI structure, in one example. The top semiconducting layer is commonly silicon when guiding IR light within waveguiding section 306, however, other semiconducting materials such as any of the combination of III-V and II-VI materials, including any of their tertiary and quaternary variants, may be used as well.

Light is guided through waveguiding section 306, according to an embodiment. In one example, waveguiding section 306 includes a ridge 312 to provide better confinement of the mode within the waveguide. Other waveguide designs are possible as well and the invention is not limited to rib waveguides as illustrated. For example, the light may be confined within a strip waveguide patterned upon a semiconducting substrate and having cladding material on some or all sides.

In an embodiment, doped section 308, doped section 310 and waveguiding region 306 form a p-i-n diode. Doped section 308 may include a $p^+$ dopant concentration while doped section 310 may include an $n^+$ dopant concentration. In one example, each doped section may include a doping concentration around $1\times10^{17}$ of either electrons or holes. Waveguiding section 306 is left substantially un-doped or intrinsic. In another example, waveguiding section 306 is lightly doped such as being at least 100 times more lightly doped than either doped section 308 or doped section 310. Each doped section is disposed on either side of waveguiding section 306 to form the p-i-n structure in the top semiconducting layer. Note that the illustrated boundaries between doped section 308 and waveguiding section 306 and between doped section 310 and waveguiding section 306 are not intended to be limiting. For example, the intrinsic section of waveguiding section 306 may be the same width as the width of ridge 312. In other examples, the boundaries extend further than illustrated and create a wider waveguiding section 306. Doped region 308 and doped region 310 may be created via various masking and ion implantation techniques as would be understood by one having ordinary skill in the art given the description herein.

In an embodiment, electro-optical phase modulator 300 includes at least two modulating regions for affecting the properties of the light propagating through waveguiding section 306. Electrodes 314a and 314b are disposed in a first modulating region while electrodes 316a and 316b are disposed in a second modulating region. The first and second modulating regions are separated by a boundary 318 as illustrated in FIG. 3. Applying an electric potential between the pair of electrodes 314a and 314b in the first modulating region causes a first modulation to the light within waveguiding region 306 due to carrier injection into waveguiding region 306. Similarly, applying an electric potential between the pair of electrodes 316a and 316b in the second modulating region causes a second modulation to the light within waveguiding region 306. The ellipses in FIG. 3 are intended to indicate that other modulating regions may be cascaded together and the invention is not limited to only having two cascaded modulating regions. The electrodes may be any suitably highly conductive material such as, for example, gold, copper, platinum, aluminum, or any alloy thereof. Additionally, it should be understood that such electrodes may include a layer structure of various conductive materials and alloys to promote better adhesion and low resistivity.

Boundary 318 between the two modulating regions may merely be an imaginary boundary. For example, the same doped section 310 and doped section 308 may extend between both modulating regions providing no definite distinction between the two modulating regions. In this case, the regions may be defined based on the E-field profile that exists between the pair of electrodes 314a and 314b, and the E-field profile that exists between the pair of electrodes 316a and 316b. In another example, the doping concentration within doped section 310 changes between the first and second modulation regions separated by boundary 318. Similarly, the doped concentration within doped section 308 may change between the first and second modulation regions separated by boundary 318.

In another embodiment, boundary 318 includes silicon trench isolation (STI) so as to electrically isolate the two modulating regions. STI may involve etching through the top semiconducting layer and filling the etched region with an insulating material, such as silicon dioxide. Boundary 318 may also include an etched trench down to at least buried insulating layer 304 to separate the two modulating regions. Another example of boundary 318 includes a doped area that has the opposite carrier concentration from the surrounding doped section 308 or 310. For example, if doped section 308 was $p^+$ doped and doped section 310 was $n^+$ doped, then boundary 318 would include a $n^+$ doped area on the side of doped section 308 and a $p^+$ doped area on the side of doped section 310. Such a potential barrier generated by oppositely doping boundary 318 may isolate the modulating regions from one another.

An example operation of electro-optical phase modulator 300 involves accurately adjusting the carrier concentration in waveguiding section 306 through each modulating region in order to change the phase and/or frequency of the guiding light such that a substantially flat amplitude response at the output is achieved (e.g., mitigate RAM). The carrier concentration may be adjusted in each modulating region by varying the applied potential to each region. That is, in an embodiment, the applied electric potentials are coordinated so that they act together to nullify any amplitude changes caused by an individually applied electric potential. Injection of electrons and holes into waveguiding section 306 produces a change in the refractive index of the material. Expressions for refractive index ($\Delta n$) and absorption ($\Delta \alpha$) changes due to injection or depletion of carriers in silicon have been produced by Soref and Bennet and described in their paper "*Electrooptical effects in silicon*", *Journal of Quantum Electronics, Vol. QE*-23, 1987, the disclosure of which is incorporated herein by reference. For example, the real part of the refractive index at a wavelength of 1.3 µm changes according to equation 1 below.

$$\Delta n = -(6.2 \times 10^{-22} \Delta N_e + 6.0 \times 10^{-18} \Delta N_h^{0.8}) \tag{1}$$

Changes in the imaginary part of the refractive index result in absorption losses and are expressed according to equation 2 below.

$$\Delta \alpha = 6.0 \times 10^{-18} \Delta N_e + 4.0 \times 10^{-18} \Delta N_h \tag{2}$$

$\Delta \alpha$ converted in dB would be $\Delta \alpha_{dB} = 10 \log(\exp(-\Delta \alpha L))$ where L is the length of the modulating region. The simulated results of the calculations are shown in FIGS. 4A and 4B. FIG. 4A illustrates the phase shift vs. varying modulator length and for various injected carrier concentrations while FIG. 4B illustrates the absorption vs. varying modulator length and also for various injected carrier concentrations.

In an embodiment, an expression for the total phase shift at the output of the various modulating regions, where M is the number of cascaded modulating regions, is given by equation 3 below.

$$\Delta \varphi(t) = \frac{2\pi}{\lambda} \sum_{i=1}^{M} \Delta n_i(N_i(t)) \cdot L_i \tag{3}$$

In Equation 3, $\lambda$ is the center emission wavelength and $\Delta n_i$, $L_i$ and $N_i(t)$ are the refractive index change, the length and the carrier injection level with the time level of the i-th modulating section. The total loss due to modulation of the refractive index in logarithmical units ($\Delta \alpha_{dB}$) is set forth as described in equation 4 below.

$$\Delta \alpha_{dB}(t) = 10 \cdot \log_{10}(e^{-\Sigma_{i=1}^{M} \Delta \alpha_i(N_i(t)) \cdot L_i}) \tag{4}$$

In equation 4, $\Delta \alpha_i$ is the loss coefficient per centimeter. According to an embodiment, once wavelength $\lambda$ is fixed, the length L and the modulating signals resulting in the carrier concentrations $N_i(t)$ of each section must be properly engineered in order to meet the design requirements in terms of both phase shift and loss.

In an embodiment, a sequence of at least two modulation regions are operated by a same triangular waveform, but with a phase difference of $\pi$ radians. As a result, the output would produce a constant amplitude attenuation and an overall phase shift of the light from 0 to $\pi$ radians as illustrated in FIG. 5. In the figure, Region 1 stands for the modulation occurring in the first modulating region while Region 2 stands for the modulation occurring in the second modulating region. The affected light, after propagating through each modulating region, will experience a phase shift and attenuation given by equations 5 and 6 below for the period of time from 0 to T.

$$const = \alpha(t) = \Delta\alpha(N_{max1}(t/T))L_1 + \Delta\alpha(N_{max2}(1 - t/T))L_2 \tag{2}$$

$$\varphi(t) = \frac{2\pi}{\lambda}(\Delta n(N_{max1}(t/T))L_1 + \Delta n(N_{max2}(1 - t/T))L_2) \tag{3}$$

In the equations above, $N_{max1}$ is the maximum number of carriers injected in the first modulator while $N_{max2}$ is the maximum amount of carriers injected in the second modulator. By introducing a parameter $$k = \frac{L_2}{L_1} = \frac{\alpha_1}{\alpha_2},$$

the phase shift may be given as shown in equation 7 below.

$$\varphi(t) = \frac{2\pi}{\lambda} L_1(\Delta n(N_{max1}(t/T)) + \Delta n(N_{max2}(1 - t/T))k) \tag{7}$$

From these expressions, the length of the first modulating region may be calculated by taking a ratio of the lengths equal to k. These models assume an absence of injection current making the amount of carriers in the waveguiding region equal to zero.

The models described above in Equations 5-7 may be simulated for a range of injected doping concentrations and values of k, to determine the lengths for each modulating region. FIGS. 6A-6C illustrate simulations using a value of 0.01 for k and for injected carrier concentrations in the first modulating region ranging from $10^{16}$ to $10^{18}$. The different lengths for each of the two modulating regions and their associated phase shifts for varying carrier injection concentrations are shown in FIGS. 6A and 6B. FIG. 6C displays the simulated results for the absorption for varying injected carrier concentrations in the first modulating region.

Additional simulation results are provided in FIGS. 7A and 7B respectively, displaying the phase shift and absorption loss in each of the two modulation regions, as well as the overall phase shift and absorption loss. The simulation results are given over a carrier concentration range from $10^{14}$ to $10^{17}$. For the simulations shown in FIGS. 7A and 7B, k=0.01 and the lengths of the two modulation regions are 4.55 mm and 45 µm (100× difference since k=0.01.) The modulation depth is 0.996π radians, which would be unity if the lower limit of the concentration of carriers was 0. The absorption remains substantially constant even for varying injected carrier concentration due to the added effects from both modulated regions, while still allowing a change in phase shift for varying injected carrier concentration.

FIGS. 8A and 8B show more simulation results when the lengths of the two modulation regions are 28.74 mm and 287 µm (100× difference since k=0.01.) The modulation depth is 0.975π radians and k=0.01. Once again, the absorption remains substantially constant while the phase shifts across varying injected carrier concentrations.

Time-varying simulations of a described embodiment of electro-optical phase modulator 300 are shown in FIGS. 9A-9C. The carrier concentration varies over time in a sawtooth type waveform having a period a and an amplitude ranging from 0 to $N_{max_i}$ as described in equation 8 below and shown in FIG. 9A. Note that sawtooth waveforms are simulated in both modulating regions and each have the same period a, however, the first modulating region has a substantially lower injected carrier concentration than the second modulating region.

$$N_i(t) = N_{max_i}\left(\frac{t}{a} - \left\lfloor \frac{1}{2} + \frac{t}{a} \right\rfloor + 1\right) \quad (8)$$

Using equations 9 and 10 below, a set of possible lengths for each modulating section as well as their associated maximum carrier concentrations ($N_{max_1}$ and $N_{max_2}$ when there are two modulating regions) can be determined.

$$\Delta\phi(t)_{max} - \Delta\phi(t)_{min} = \pi \quad (9)$$

$$\Delta\alpha_{dB}(t)_{max} - \Delta\alpha_{dB}(t)_{min} = 0 \quad (10)$$

In the simulated example shown in FIGS. 9A-9C, the lengths are 1 mm and 10 μm for the first and second regions respectively with $N_{max_1}=6.7429\cdot10^{17}$ cm$^{-3}$ and $N_{max_2}=6.7429\cdot10^{19}$ cm$^{-3}$. Other lengths and carrier concentrations are also possible when creating a sawtooth profile as long as the conditions of equations 9 and 10 are met. Furthermore, any number of modulating regions (M) may be cascaded using the relationship $\Sigma_{i=1}^{M} N_{max_i} \cdot L_i = 0$.

FIGS. 9B and 9C show how the varying carrier concentration over time in each modulating region results in a substantially flat loss characteristic over time (e.g., null RAM), and a nearly sawtooth waveform for the phase change over time. In particular, the total loss caused by the refractive index modulation has reached 2.92 dB in this example. The sawtooth waveform in the total phase shift substantially follows the sawtooth waveform in the generated carrier concentration over time. The sawtooth waveform observed in the phase shift is non-linear due to the non-linear dependence of Δα on the carrier density level. Any arbitrary waveform may be chosen to act as a modulating signal to achieve a substantially null RAM so long as the relation $$\frac{d\Delta\alpha_{dB}(t)}{dt} = 0$$

is fulfilled.

Various embodiments of electro-optical phase modulator 300 may be used within an optical system such as, for example, an OCT system. FIG. 10 illustrates an example OCT system 1001, utilizing a delay unit 1012, and used for imaging a sample 1010, according to an embodiment. Delay unit 1012 may include various light modulating elements, such as electro-optical phase modulator 300. These modulating elements may perform phase and/or frequency modulation to counteract undesired optical effects in the light such as birefringence. The use of the term "light" may refer to any range of the electromagnetic spectrum. In an embodiment, the term "light" refers to infrared radiation at a wavelength of around 1.3 μm.

OCT system 1001 further includes an optical source 1002, a splitting element 1004, a sample arm 1006, a reference arm 1008, and a detector 1014. In the embodiment shown, delay unit 1012 is located within reference arm 1008. However, it should be understood that delay unit 1012 may instead be located in sample arm 1006. Alternatively, various elements of delay unit 1012 may be present in both sample arm 1006 and reference arm 1008. For example, elements of delay unit 1012 that introduce a variable delay to the light may be located in sample arm 1006 while elements that modulate different polarization modes of the light using embodiments of electro-optical phase modulator 300 described herein may be located in reference arm 1008. In one example, sample arm 1006 and reference arm 1008 are optical waveguides such as patterned waveguides or optical fibers. In an embodiment, all of the components of OCT system 1001 are integrated onto a planar lightwave circuit (PLC). In another embodiment, at least all the components within delay unit 1012 are integrated on the same substrate of a PLC. Other implementations may be considered as well, such as, for example, fiber optic systems, free-space optical systems, photonic crystal systems, etc.

It should be understood that OCT system 1001 may include any number of other optical elements not shown for the sake of clarity. For example, OCT system 1001 may include mirrors, lenses, gratings, splitters, micromechanical elements, etc., along the paths of sample arm 1006 or reference arm 1008.

Splitting element 1004 is used to direct light received from optical source 1002 to both sample arm 1006 and reference arm 1008. Splitting element 1004 may be, for example, a bi-directional coupler, an optical splitter, or any other modulating optical device that converts a single beam of light into two or more beams of light.

Light that travels down sample arm 1006 ultimately impinges upon sample 1010. Sample 1010 may be any suitable sample to be imaged, such as tissue. During an OCT procedure, the light scans at a certain depth within sample 1010 and the scattered radiation is collected back into sample arm 1006. In another embodiment, the scattered radiation is collected back into a different waveguide than the transmitting waveguide. The scan depth may be chosen via the delay imposed on the light within delay unit 1012.

Light within sample arm 1006 and reference arm 1008 is recombined before being received at detector 1014. In the embodiment shown, the light is recombined by splitting element 1004. In another embodiment, the light is recombined at a different optical coupling element than splitting element 1004.

An example method 1100 is described for modulating a beam of radiation, according to an embodiment. The steps of method 1100 may be performed by various elements of an electro-optical phase modulator, such as electro-optical phase modulator 300 illustrated in FIG. 3. It is to be understood that the order of method 1100 is not intended to be limiting and that the steps may be performed in any order to produce the substantially same result.

At block 1102, a beam of radiation is guided through a waveguide. The waveguide may be a rib waveguide as illustrated in FIG. 3, or any other type of waveguide.

At block 1104, a first electric potential is applied to a first region associated with the waveguide. The first electric potential may be applied across a first set of electrodes patterned within the first region. The first electric potential causes a first modulation to the beam of radiation due to carrier injection into the waveguide section where the beam of radiation is substantially contained. In one example, the first electric potential is applied to create a sawtooth profile of the carrier density over time within the first region. Barring any further modulation, the beam of radiation may exhibit a residual amplitude modulation (RAM) after traversing the first region.

At block 1106, a second electric potential is applied to a second region associated with the waveguide and cascaded with the first region. The second electric potential may be applied across a second set of electrodes patterned within the second region. The second electric potential causes a second modulation to the beam of radiation due to carrier injection into the waveguide section where the beam of radiation is substantially contained. In one example, the second electric potential creates a sawtooth profile of the carrier density having substantially the same period, but a different amplitude than the sawtooth profile of the carrier density created in the first region. In an embodiment, the application of both the first electric potential and the second electric potential causes substantially null residual amplitude modulation of the beam of radiation.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An electro-optical modulator comprising:
a waveguide on a substrate, and configured to guide a beam of radiation, wherein the beam of radiation travels in a first direction along a length of the waveguide;
a first region on the substrate, the first region having a length parallel to the first direction, wherein a first electric potential applied to the first region causes a first phase modulation to the beam of radiation; and
a second region on the substrate, the second region having a length parallel to the first direction, wherein a second electric potential applied to the second region causes a second phase modulation to the beam of radiation different from the first phase modulation,
wherein the first electric potential, the length of the first region, the second electric potential, and the length of the second region are determined such that the first phase modulation combined with the second phase modulation provides substantially null residual amplitude modulation of the beam of radiation.

2. The electro-optical modulator of claim 1, wherein the substrate uses silicon-on-insulator (SOI) technology.

3. The electro-optical modulator of claim 1, wherein the first phase modulation and the second phase modulation cause a change in a frequency of the beam of radiation.

4. The electro-optical modulator of claim 1, wherein the waveguide comprises a semiconducting material.

5. The electro-optical modulator of claim 1, wherein the first region comprises a first n-doped region and a first p-doped region, and the first electric potential is applied between the first n-doped region and the first p-doped region.

6. The electro-optical modulator of claim 5, wherein the second region comprises a second n-doped region and a second p-doped region, and the second electric potential is applied between the second n-doped region and the second p-doped region.

7. The electro-optical modulator of claim 6, wherein the first n-doped region and the second n-doped region have a same dopant concentration, and the first p-doped region and the second p-doped region have a same dopant concentration.

8. The electro-optical modulator of claim 5, wherein the waveguide comprises substantially undoped silicon and is sandwiched between the first n-doped and first p-doped regions.

9. The electro-optical modulator of claim 1, wherein the waveguide is a rib waveguide.

10. The electro-optical modulator of claim 1, wherein the second region is cascaded with the first region.

11. The electro-optical modulator of claim 1, wherein the first and second regions are separated on the substrate using silicon trench isolation (STI).

12. The electro-optical modulator of claim 1, further comprising a doped region on the substrate that separates the first region from the second region.

13. An electro-optical modulator comprising:
a waveguide configured to guide a beam of radiation;
a first region associated with the waveguide, wherein a first electric potential applied to the first region causes a first modulation to the beam of radiation; and
a second region associated with the waveguide, wherein a second electric potential applied to the second region causes a second modulation to the beam of radiation,
wherein the first modulation combined with the second modulation provides substantially null residual amplitude modulation of the beam of radiation,
wherein the waveguide comprises a semiconducting material, and
wherein at least one of the first electric potential and second electric potential generate a sawtooth carrier density profile in the semiconducting material that varies with time.

14. An electro-optical modulator comprising:
a waveguide on a substrate, and configured to guide a beam of radiation, wherein the beam of radiation travels in a first direction along a length of the waveguide; and
a plurality of regions on the substrate, each region of the plurality of regions having a length parallel to the first direction, wherein a separate electric potential is applied to each region of the plurality of regions, causing a respective phase modulation to the beam of radiation, and wherein each of the separate electric potentials and the length of each region are determined such that the combination of each respective phase modulation provides substantially null residual amplitude modulation of the beam of radiation.

15. An optical coherence tomography system comprising:
an optical source configured to provide a beam of radiation;
an optical element configured to split the beam of radiation between at least a first waveguide and a second waveguide, wherein a first portion of the beam of radiation propagates through the first waveguide and a second portion of the beam of radiation propagates through the second waveguide, wherein the first waveguide is on a substrate, and wherein the first portion of the beam of radiation travels in a first direction along a length of the first waveguide; and an electro-optical modulator comprising:
- a first region on the substrate, the first region having a length parallel to the first direction, wherein a first electric potential applied to the first region causes a first phase modulation to the first portion of the beam of radiation, and
- a second region on the substrate, the second region having a length parallel to the first direction, wherein a second electric potential applied to the second region causes a second phase modulation to the first portion of the beam of radiation,
- wherein the first electric potential, the length of the first region, the second electric potential, and the length of the second region are determined such that the first phase modulation combined with the second phase modulation provides substantially null residual amplitude modulation of the first portion of the beam of radiation.

16. A method of modulating a beam of radiation, comprising:
- providing a waveguide on a substrate, the waveguide configured to guide the beam of radiation in a first direction along a length of the waveguide;
- providing a first region on the substrate, the first region having a length parallel to the first direction;
- applying a first electric potential to the first region, the first electric potential applying a first phase modulation to the beam of radiation;
- providing a second region on the substrate, the second region being cascaded with the first region and having a length parallel to the first direction; and
- applying a second electric potential to the second region, the second electric potential applying a second phase modulation to the beam of radiation,
- wherein the length of the first region, the length of the second region, a value of the first electric potential, and a value of the second electric potential are selected such that the first phase modulation and the second phase modulation cause a substantially null residual amplitude modulation of the beam of radiation.

17. An electro-optical modulator comprising:
- a waveguide on a substrate, and configured to guide a beam of radiation having an amplitude and a frequency, wherein the beam of radiation travels in a first direction along a length of the waveguide;
- a first region on the substrate, the first region having a length parallel to the first direction, wherein a first electric potential applied to the first region causes a residual amplitude modulation of the beam of radiation; and
- a second region on the substrate, the second region having a length parallel to the first direction, wherein the length of the second region and a second electric potential applied to the second region are chosen to achieve substantially null residual amplitude modulation of the beam of radiation, and wherein both the first electric potential and the second electric potential cause a modulation in a phase of the beam of radiation.

* * * * *